United States Patent [19]
Saper et al.

[11] Patent Number: 5,090,410
[45] Date of Patent: Feb. 25, 1992

[54] FASTENER FOR ATTACHING SENSOR TO THE BODY

[75] Inventors: Lawrence Saper, New York, N.Y.; Bruce L. Hanson, Franklin Lakes, N.J.

[73] Assignee: Datascope Investment Corp., Montvale, N.J.

[21] Appl. No.: 372,316

[22] Filed: Jun. 28, 1989

[51] Int. Cl.$^5$ .............................................. A61B 5/00
[52] U.S. Cl. .................................. 128/633; 128/664; 128/665; 356/41
[58] Field of Search ............... 128/633, 640, 632, 635, 128/636, 637, 639, 641, 643, 644, 731, 82.1, 802, 687, 672, 664, 691, 667, 736; 356/41; 604/305, 308, 307

[56] References Cited

U.S. PATENT DOCUMENTS

| | | | |
|---|---|---|---|
| 3,215,265 | 11/1965 | Welin-Berger | 128/736 |
| 4,144,889 | 3/1979 | Tyers et al. | 128/419 P |
| 4,179,944 | 4/1980 | Catlin | 128/736 |
| 4,213,463 | 7/1980 | Osenkarski | 128/639 |
| 4,243,051 | 1/1981 | Wittemann | 128/802 |
| 4,743,232 | 5/1988 | Kruger | 604/307 |
| 4,825,872 | 5/1989 | Tan et al. | 128/633 |
| 4,825,879 | 5/1989 | Tan et al. | 128/633 |
| 4,865,638 | 9/1989 | Rich et al. | 128/633 |

Primary Examiner—Stephen C. Pellegrino
Attorney, Agent, or Firm—Fitzpatrick, Cella, Harper & Scinto

[57] ABSTRACT

A bandage for attaching a sensor to a part of the human body while protecting the sensor against contamination and permitting its reuse in which the sensor is located within a flexible transparent sleeve which is fastened to the adhesive inner surface of the bandage, the parts of the bandage inner adhesive surface outside of the sleeve thereafter being fastened to the body. In the preferred embodiment the probe is an oximeter probe with a light emitter and a light detector. Apertures are provided in the bandage to view the positioning of the oximeter components.

16 Claims, 1 Drawing Sheet

FIG. 1.
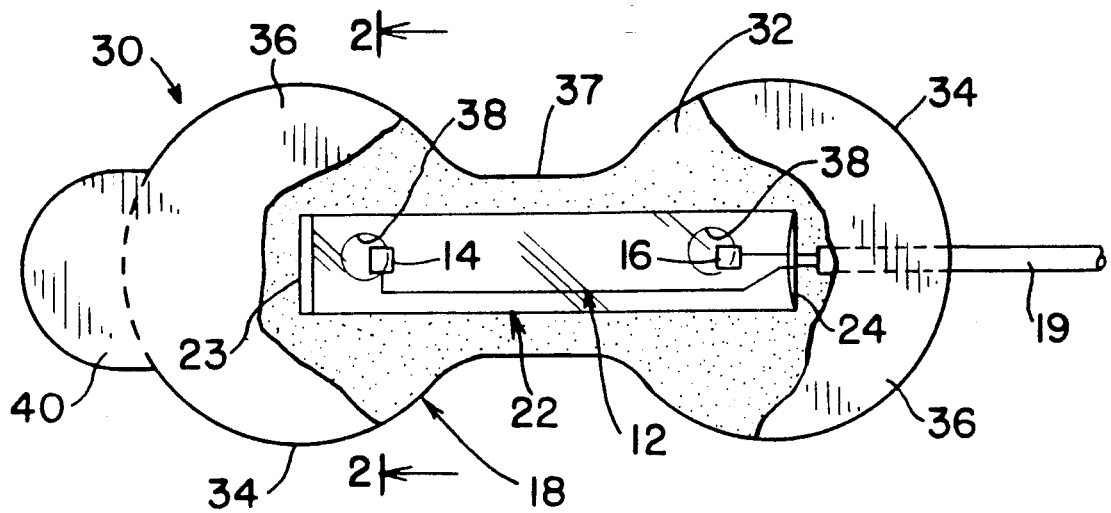
FIG. 2.
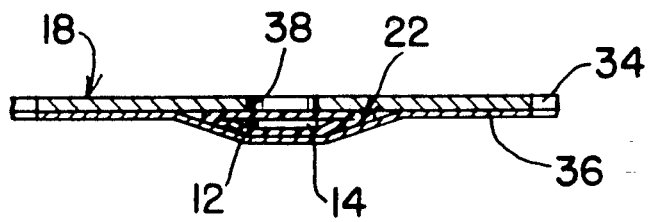
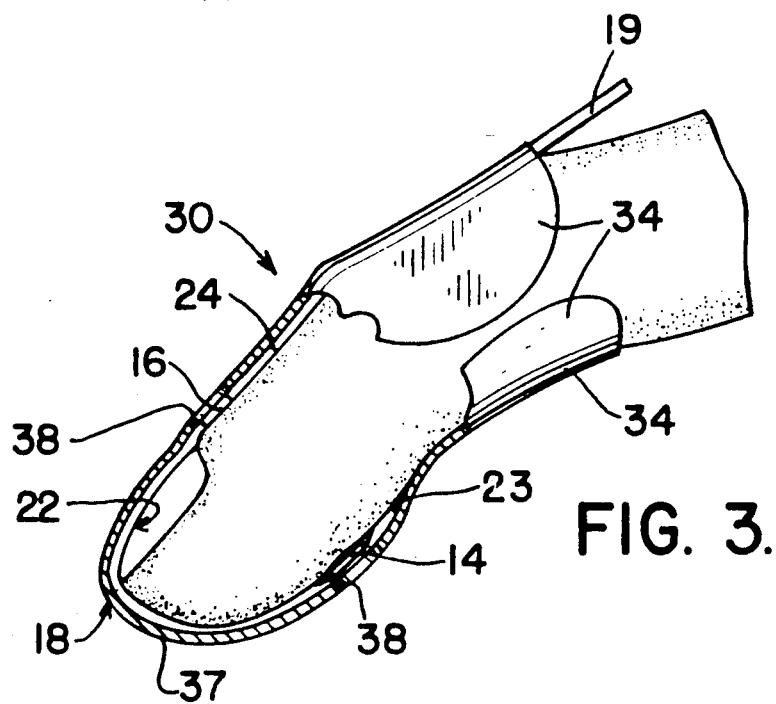
FIG. 3.

FASTENER FOR ATTACHING SENSOR TO THE BODY

BACKGROUND OF THE INVENTION

Various types of sensors often must be attached to a human body for medical examination or monitoring purposes. Such sensors include, example, temperature sensors and also sensors for use in oximetry. Usually, the sensor must be held close to or in direct contact with the body for a period of time.

For example, in the case of an oximetry sensor, wherein oximetry is used as a non-invasive method of determining the oxygen saturation of a patient's blood, an oximeter probe is used. Such a probe is a rather sophisticated miniaturized device having two components mounted on a member, a sensor at one end and an a light emitting source, such as an LED, at the other end. The mounting member is folded around a part of the patient's body, such as a finger or possibly the earlobe, with the sensor and light source at predetermined locations so that the emitted light from the source can pass through the patient's body tissue to the sensor. It is thereafter taped in place by adhesive tape, or held in place with a belt, strap or clamps. The character of the light received by the sensor is subject to change by the "color" of the patient's blood which is an indication of its oxygen content.

While strapping, the use of clamps, Velcro type bandages or taping of a probe or other type of sensor to the patient's body are workable, these approaches have problems in that they are sometimes difficult to apply to the body while holding the probe or other sensor at the proper locations. In the case of an oximeter probe which comprises the two components discussed above, it is also difficult to locate the sensor and the light source at the proper location and hold them there during the taping or clamping.

In addition, an oximeter probe is expensive. Therefore, it is not intended to be disposable and it is to be reused. The prior art methods and apparatus for attachment of the sensor make this goal difficult to achieve since parts of the probe and light emitting source come into contact with the patient's body, body fluids, etc. This gives rise to a sterilization problem, i.e., the probe components must be sterilized for reuse since they come in contact with the body. Also, where tape is used to fasten the probe to the body, the components are subject to having a residue of adhesive left on them.

Similar problems occur, for example, in using various types of temperature sensor probes which must be fastened to predetermined portions of the body and are also not intended to be disposable.

BRIEF DESCRIPTION OF THE INVENTION

The present invention relates to a novel arrangement for quickly attaching a sensor to a part of the body while accurately locating it. In addition, the attachment is carried out in such a manner that the sensor is protected from direct contact with the body blood, body fluids, adhesive tape residue, etc. This eliminates the need for sterilization and cleaning. It also preserves the sensor and other parts of the probe for multiple usage thereby saving the time and effort normally expanded in cleaning the probe between patients.

In accordance with the invention, the sensor is located within a sleeve and the sleeve is attached to an adhesive bandage. The bandage is adapted to be wrapped around the appropriate part of the patient's body and fastened thereto with the sensor in the appropriate location. In the case of an oximeter probe, which has both a sensor and a light source, both components are within the sleeve which is attached to the bandage. When the bandage is applied to the patient's body, the components are substantially located in the correct position. When the bandage is fastened to the human body, the bandage adhesive anchors the leads from the sensor against the patient's body to make them more stable. This makes the electrical connection more reliable and less sensitive to breakage. When the bandage is removed from the patient's body, the sleeve containing the sensor, can be detached from the adhesive part of the bandage. The sleeve can then be disposed of and the sensor placed into a new sleeve. The sensor does not have to be pre-sterilized since it neither came into contact with the body nor the adhesive of the bandage.

In a preferred embodiment of the invention related to an oximeter probe, the components of the probe are placed within the sleeve and the sleeve fastened to the bandage. The bandage preferably has a hole opposite the location where each of the components, the light source and the sensor, are to be located so that proper location of the components on the patient's body is assured. That is, when the bandage is fastened to the patient's body, the holes provide a visual alignment guide for the components.

OBJECTS OF THE INVENTION

It is therefore an object of the present invention to provide a bandage for attaching a sensor to a part of the human body with the sensor being protected during the time of attachment and use.

An additional object is to provide attaching means for a sensor which needs to be attached to a part of the human body by an adhesive bandage, with the sensor being protected within a sleeve which attached to an adhesive part of the bandage.

A further object is to provide a bandage for attaching an oximeter probe to the human body with the components of the probe being within a sleeve fastened to an adhesive bandage which is to be fastened to the body.

Still a further object is to provide a bandage for attaching an oximeter probe to a part of the human body in which the sensor and light source of the probe are contained within a sleeve mounted to an adhesive part of the bandage and the bandage has openings through which the probe components can be aligned.

BRIEF DESCRIPTION OF THE DRAWINGS

Other objects and advantages of the present invention will become more apparent upon reference to the following specification and annexed drawings in which:

FIG. 1 is a plan view of the bandage in accordance with the invention;

FIG. 2 is a cross-sectional view taken along lines 2—2 of FIG. 1; and

FIG. 3 is a view, partly broken away, showing the bandage attached to a part of the human body.

DETAILED DESCRIPTION OF THE INVENTION

Referring to FIGS. 1 and 2, the preferred embodiment is described relative to applying and fastening an oximeter probe 12. The probe has two primary components, a light emitter 14, such as a light emitting diode (LED), and a light sensor 16, attached to cables (leads) 19. The leads 19 exit from one end of the probe 12. Such oximeter probes are well known in the art and do not, in themselves, form the present invention.

In accordance with the invention, the probe 12 is contained within a sleeve 22 which is of a transparent flexible material which is impermeable to body fluid, e.g., a plastic such as polyethylene. One end of the sleeve can be sealed, such as shown at 23. The cable or lead wires 19 from the oximeter probe extend through the sleeve's other end 24 which is open.

The bandage 30 has an adhesive inner surface 32 and an outer surface which is preferably non-adhesive. The bandage 30 can be of a desired length or shape. In the preferred embodiment of the invention described, where the bandage as to be fastened to a finger, it has a generally butterfly shape with two wings 34 extending from a central connecting part 37.

A piece 36 of a non-adhesive backing paper of a shape generally conforming to that of the adhesive part of bandage 30 is placed over the adhesive inner surface 32. The backing paper 36 is preferably of the release type so it can be easily removed. This protects the adhesive inner surface 32 of the bandage prior to its use. The protective paper backing 36 is peeled off when it comes time to use the bandage. It is preferred that the sleeve 22 with the probe 12 therein be attached to the adhesive surface before the paper backing is applied.

As seen best in FIG. 3, each of the bandage wings 34 has a hole 38 therein. The hole is preferably located to have a distance therebetween corresponding to the distance between light emitter 14 and the light sensor 16. Since the end 24 of the sleeve 22 is open, the cable 19 can be manipulated to position the probe strip 12 and its components within the sleeve 22, that is, one of the components 16, 14 is to be opposite each of the holes 38.

In using the bandage, the sleeve 22 containing the probe 12 and its components is first attached to the bandage inner adhesive surface 32. The backing paper 36 is placed thereover so that the bandage with the probe therein can be shipped, stored, etc. Alternatively, if a sleeve 22 with the probe 12 therein is to be attached to the inner surface 32 just prior to use, the paper backing 36 is peeled off and this is done.

The bandage wings 34 are now wrapped around the part of the patient to which the bandage is being fastened, this being shown as the finger, so that the light emitting source 14 is on one side of the finger and the light sensor 16 on the other side. Since the sleeve 22 and the strip 18 on which the two probe components are flexible, they conform to the part of the body around which the bandage is wrapped. The holes 38 permit alignment of the light emitter and sensor relative to the finger by the person applying the bandage. That is, the person can visualize a line generally transverse to the part of the body to which the bandage is applied extending through the two holes 38. When this is done, the light emitter and the sensor are relatively well aligned. The light emitting diode 14 has a somewhat dispersive pattern, i.e., it is generally conical and exact alignment of the light emitter and the sensor transverse to the body part is not exactly needed. However, this general alignment arrangement cannot be departed from by a very great amount.

The cable 19 emerges from under the adhesive portion of the wing and is connected to the oximeter instrument (not shown). The adhesive surface serves to anchor the cable 19 to the finger, thereby preventing damage to the connection between the cable and the probe which might be caused by inadvertent patient movement.

At the end of the use of the probe, the bandage is removed from the patient's finger in the same manner as any adhesive bandage would be. The probe 12 is then removed from the transparent protective sleeve 22 for inspection and reuse. It does not have to be sterilized since it never came into contact with the body. The bandage is disposed of and the probe can be inserted into a new sterile sleeve which can be attached to a new bandage.

While the invention has been described with respect to an oximeter probe, it should be understood that it is equally applicable to other types of sensors, for example, temperature sensors, etc. In any case, the sensor itself is protected by the sleeve and it can be removed from the sleeve for inspection and reuse by inserting it into another sleeve which is to be fastened to another bandage. Also, while the bandage has been shown as of generally butterfly in shape, it should be understood that other shapes in a variety of sizes can be used, e.g., strips, ovals, square or rectangular pads, etc.

As should be apparent that the novel bandage for fastening a sensor to a part of the human body has been disclosed in which the elements of the sensor are protected and can be reused.

We claim:

1. A disposable sleeve and bandage for attachment to a patient wherein said sleeve is adapted to accept therein a probe, comprising:
   a generally planar flexible bandage strip having adhesive on at least a portion of one face thereof;
   a sleeve having an opening therein adapted to receive said probe, wherein said probe can slide through said opening into said sleeve and wherein said probe can be removed from said sleeve by sliding it therefrom;
   wherein said sleeve includes means for preventing said probe from contacting said patient when said probe is resident in said sleeve and means for preventing said probe from contacting said adhesive;
   locating means in the strip for positioning said probe in said sleeve.

2. The sleeve and bandage of claim 1 wherein said sleeve is generally rectangular in shape to receive slidably therein an elongated probe having a generally rectangular cross section.

3. The sleeve and bandage of claim 1 wherein said sleeve has a front sheet and a back sheet and wherein said means for preventing contact with said patient comprises said front sheet.

4. The sleeve and bandage of claim 1 wherein said sleeve has two ends, one end being closed and the other end being open and wherein said probe is adapted to slide into and out of said sleeve.

5. The sleeve and bandage of claim 4 wherein said sleeve is adapted to receive therein an oximeter probe.

6. The sleeve and bandage of claim 5 wherein said probe has at least one light emitting source and one light detecting sensor.

7. The sleeve and bandage of claim 6 wherein at least a portion of a face of said sleeve is transparent.

8. The sleeve and bandage of claim 7 wherein, when said probe is resident in said sleeve, said light source emits light through a transparent face portion of said sleeve and said light sensor detects light which has passed through a transparent face portion of said sleeve.

9. The sleeve and bandage of claim 6 wherein said sleeve is adapted to fold into a generally U shape about an appendage to the human body and wherein said adhesive on said face is adapted to hold said sleeve in said U shape on said appendage.

10. The sleeve and bandage of claim 9 where said sleeve is adapted to be folded into said U shape while said probe is resident in said sleeve.

11. The sleeve and bandage of claim 10 wherein said U shape fold and said adhesive attachment about said appendage substantially prevent movement of said probe relative to said sleeve and relative to said appendage.

12. The sleeve and bandage of claim 11 wherein when in said U shape, said light source is in one leg of said U and said light sensor is in the other leg of said U and wherein said U shape fold and said adhesive attachment about said appendage maintain said light source in juxtaposition to said light sensor.

13. The sleeve and bandage of claim 12 wherein, when in said adhesively secured U shape, said light source emits light rays at least some of which pass through said appendage before reaching said light sensor.

14. The sleeve and bandage of claim 10 wherein said bandage strip and sleeve are adapted to be removed from said appendage and wherein said sleeve is adapted to be unfolded and wherein said probe can be removed from said sleeve following said unfolding.

15. The sleeve and bandage of claim 10 wherein at least a portion of a face of said sleeve is transparent and wherein when in said U shape, said light source is located in one leg of said U and wherein said light sensor is located in the other leg of said U and is positioned to receive light rays emitted from said light source.

16. The sleeve and bandage of claim 9 wherein said locating means are adapted to indicate proper positioning of said probe on said appendage.

* * * * *

UNITED STATES PATENT AND TRADEMARK OFFICE
CERTIFICATE OF CORRECTION

PATENT NO. : 5,090,410
DATED : February 25, 1992
INVENTOR(S) : Lawrence Saper et al It is certified that error appears in the above-indentified patent and that said Letters Patent is hereby corrected as shown below:

On the title page, Item

AT [56] REFERENCES CITED

U.S. Patent Documents,
"4,865,638" should read --4,865,038-- and
"4,179,944" should read --4,197,944--.

COLUMN 1

Line 8, "example," should read --for example,--.
Line 17, "an" should be deleted.

COLUMN 2

Line 14, "sensor," should read --sensor--.
Line 18, "nor" should read --nor with--.
Line 21, "fastened" should read --is fastened--.
Line 39, "attached" should read --is attached--.

COLUMN 3

Line 50, "components" should read
--components are located--.

COLUMN 4

Line 42, "adhesive;" should read --adhesive; and--.
Line 56, "sleeve." should read
--sleeve through said open end.--.
Line 57, "claim 4" should read --claim 1--.

UNITED STATES PATENT AND TRADEMARK OFFICE
CERTIFICATE OF CORRECTION

PATENT NO. : 5,090,410

DATED : February 25, 1992

INVENTOR(S) : Lawrence Saper et al

It is certified that error appears in the above-indentified patent and that said Letters Patent is hereby corrected as shown below:

COLUMN 5

Line 1, "claim 6" should read --claim 1--.
    Line 6, "where" should read --wherein--.

COLUMN 6

Line 9, "can be removed" should read --is removable--.
    Line 12, "transparent and" should read
        --transparent, wherein when in said U shape,
        said sleeve has two legs, and--.

Signed and Sealed this

Third Day of August, 1993

Attest:

MICHAEL K. KIRK

*Attesting Officer*      *Acting Commissioner of Patents and Trademarks*